United States Patent [19]

Ohno et al.

[11] Patent Number: 5,047,171
[45] Date of Patent: Sep. 10, 1991

[54] OPTICALLY ACTIVE-2,5-DIPHENYLPYRIDINE

[75] Inventors: Kouji Ohno; Shinichi Saito; Hiromichi Inoue, all of Kanagawa, Japan

[73] Assignee: Chisso Corporation, Ohsaka, Japan

[21] Appl. No.: 240,584

[22] Filed: Sep. 1, 1988

[30] Foreign Application Priority Data

Sep. 3, 1987 [JP] Japan .................. 62-220824

[51] Int. Cl.$^5$ .................. C09K 19/34; C07D 211/70; C07D 211/72
[52] U.S. Cl. .................. 252/299.61; 252/299.6; 252/299.01; 546/330; 546/342; 546/339; 546/346; 546/348; 546/350; 359/104
[58] Field of Search .......... 252/299.01, 299.5, 299.61; 350/350 R, 350 S; 546/330, 342, 339, 346, 348, 350

[56] References Cited

U.S. PATENT DOCUMENTS

| | | | |
|---|---|---|---|
| 4,684,477 | 8/1987 | Sugimori et al. | 252/299.61 |
| 4,752,413 | 6/1988 | Inoue et al. | 252/299.61 |
| 4,764,619 | 8/1988 | Gunjima et al. | 252/299.63 |
| 4,765,924 | 8/1988 | Inoue et al. | 252/299.61 |
| 4,772,416 | 9/1988 | Goto et al. | 252/299.61 |
| 4,781,857 | 11/1988 | Inoue et al. | 252/299.61 |
| 4,784,792 | 11/1988 | Inoue et al. | 252/299.61 |
| 4,818,430 | 4/1989 | Saito et al. | 252/299.61 |
| 4,880,936 | 11/1989 | Sasaki et al. | 546/339 |
| 4,900,472 | 2/1990 | Miyazawa et al. | 252/299.61 |
| 4,900,473 | 2/1990 | Miyazawa et al. | 252/299.61 |
| 4,973,425 | 11/1990 | Kazuhiko et al. | 252/299.61 |
| 4,973,426 | 11/1990 | Ohno et al. | 252/299.61 |
| 4,985,172 | 1/1991 | Wingen et al. | 252/299.61 |
| 4,997,942 | 3/1991 | Osawa et al. | 252/299.61 |

FOREIGN PATENT DOCUMENTS

| | | | |
|---|---|---|---|
| 211646 | 2/1987 | European Pat. Off. | 252/299.61 |
| 267758 | 5/1988 | European Pat. Off. | 252/299.61 |
| 0284093 | 9/1988 | European Pat. Off. | 252/299.61 |
| 3515373 | 11/1986 | Fed. Rep. of Germany | 252/299.61 |
| 3600052 | 7/1987 | Fed. Rep. of Germany | 252/299.61 |
| 61-215373 | 9/1986 | Japan | 252/299.61 |
| 87/05017 | 8/1987 | World Int. Prop. O. | 252/299.61 |
| 8705018 | 8/1987 | World Int. Prop. O. | 252/299.61 |

OTHER PUBLICATIONS

Schubert, H., Wiss. Z. Univ. Halle XIX'70 M, H.5, 5.1-18.

Demus, D., et al., Flussige Kristalle in Tabellen, Veb Deutscher Verlag fur Grumastoff Industrie, Leipzig, pp. 254-255, (1974).

Gray, G. W., et al., Liquid Crystals & Plastic Crystals, vol. 1, John Wiley & Sons, Inc., N.Y., pp. 142-143, (1974).

Primary Examiner—Robert L. Stoll
Assistant Examiner—Richard Treanor
Attorney, Agent, or Firm—Wenderoth, Lind & Ponack

[57] ABSTRACT

A liquid crystal compound suitable as a material for ferroelectric liquid crystal display elements and a liquid crystal composition containing the same are provided, which liquid crystal compound is an optically active-2,5-diphenylpyridine expressed by the formula.(I)

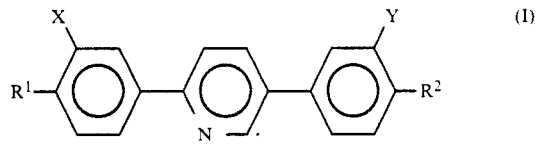

wherein one of $R^1$ and $R^2$ is 1-20C alkenyl, alkynyl, alkoxy, alkenyloxy or alkynyloxy and the other is an optically active group; and X and Y each independently represent H, halogen or CN and at least one of X and Y is H.

14 Claims, No Drawings

OPTICALLY ACTIVE-2,5-DIPHENYLPYRIDINE

BACKGROUND OF THE INVENTION

1. Field of the Invention

This invention relates to an optically active-2,5-diphenylpyridine and a liquid crystal composition containing the same. More particularly it relates to an optically active-2,5-diphenylpyridine as a chiral liquid crystal compound having an optically active group and a chiral liquid crystal composition containing the same. The liquid crystal compound referred to herein includes not only those which are observed to exhibit a liquid crystal state even in the case of use of a single compound, but also those which are observed to exhibit no liquid crystal phase in the case of a single compound, but have a similar structure to that of the above and are useful as a constituent of liquid crystal compositions.

DESCRIPTION OF THE RELATED ART

At present, TN (Twisted Nematic) display mode has been most broadly employed for liquid crystal display elements. Liquid crystal display elements employing this TN liquid crystal display have a number of advantages such as low driving voltage, small power consumption, etc., but they are inferior in the aspect of response rate to emissive display elements such as those of cathode ray electrode display, electroluminescence display, plasma display, etc. A new TN mode display element having the twist angle increased to 180°–270° has also been developed, but it is still inferior in the aspect of response rate.

As described above, various efforts for improvement have been made, but compounds having a high response rate have not yet been realized. However, a novel display mode using ferroelectric liquid crystals the research of which has recently been extensively conducted has a possibility of notably improving the response rate (Clark et al; Applied Phys. lett., 36, 899 (1980)). This mode utilizes chiral smectic phases such as chiral smectic C phase (hereinafter abbreviated to SC*) exhibiting ferroelectric properties. It has been known that phases exhibiting ferroelectric properties are not limited to SC* phase, but chiral smectic F, G, H, I, etc. phases also exhibit ferroelectric properties.

A number of superior characteristics have been required for materials practically used for ferroelectric liquid crystal display elements, but at present, no single compound can satisfy the characteristics; hence it is necessary to use ferroelectric liquid crystal compositions obtained by mixing some liquid crystal compounds or mixing liquid crystal compounds with non-liquid crystal compounds.

SUMMARY OF THE INVENTION

The object of the present invention, is to provide a liquid crystal compound suitable as a material for the above ferroelectric liquid crystal display elements and a liquid crystal composition containing the same The present invention resides in an optically active-2,5-diphenylpyridine expressed by the formula (I)

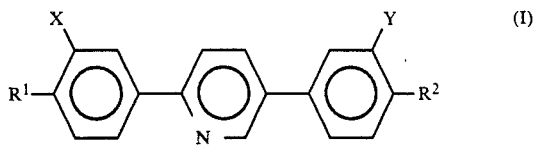

wherein one of $R^1$ and $R^2$ represents an alkyl group, an alkenyl group, an alkynyl group, an alkoxy group, an alkenyloxy group or an alkynyloxy group each of 1 to 20 carbon atoms and the other thereof represents an optically active group; and X and Y each independently represent a hydrogen atom, a halogen atom or cyano group and at least one of X and Y represents a hydrogen atom, and a ferroelectric liquid crystal composition containing the compound.

DETAILED DESCRIPTION OF PREFERRED EMBODIMENTS

Preferred examples of the optically active group as one of $R^1$ and $R^2$ are those shown in the following (a)–(f):

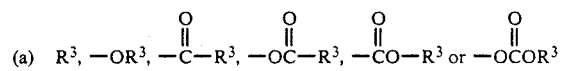

wherein $R^3$ represents an alkyl group, an alkenyl group or an alkynyl group each of 4 to 15 carbon atoms having a methyl or ethyl branch;

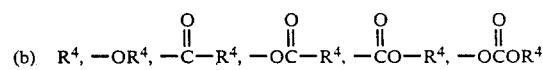

wherein $R^4$ represents an optically active halogenated alkyl group or cyanogenated alkyl group, alkenyl group or alkynyl group, each of 2 to 15 carbon atoms;

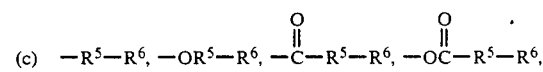

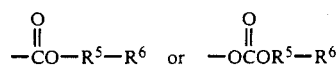

wherein $R^5$ represents an optically active alkylene group of 2 to 12 carbon atoms and $R^6$ represents an alkoxy group, an alkanoyl group, an alkanoyloxy group, an; alkoxycarbonyl group or an alkoxycarbonyloxy group each of 1 to 12 carbon atoms;

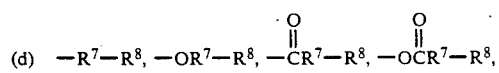

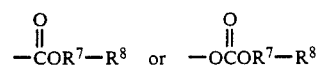

wherein $R^7$ represents an optically inactive alkylene group of 2 to 12 carbon atoms and $R^8$ represents a group expressed by

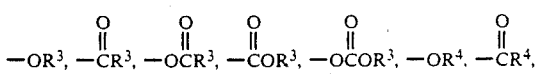

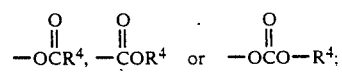

(e) 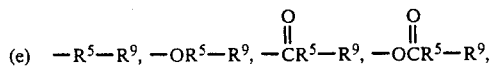
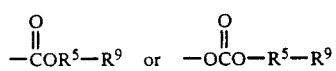
wherein $R^9$ represents $R^8$ or a group expressed by
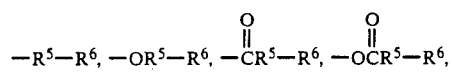
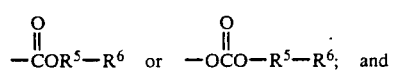 and
(f) Other groups.
Concrete examples of the groups listed in the above (a) to (f) are as follows:
as $R^3$ of the above (a),
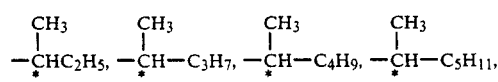
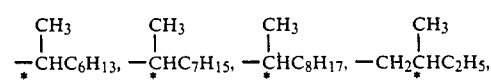
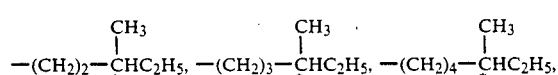
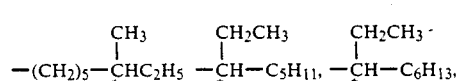
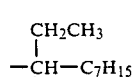
as $R^4$ of the above (b),
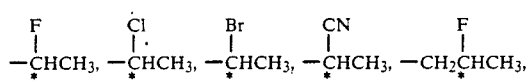
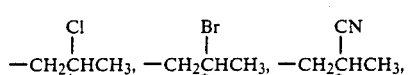
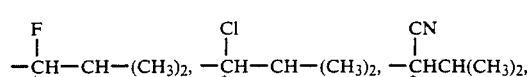
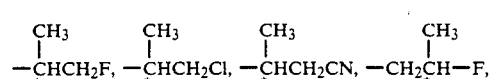
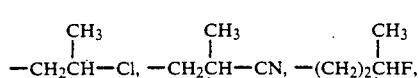
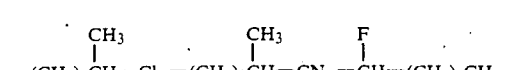
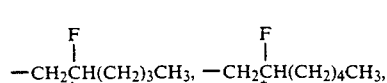
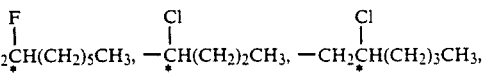
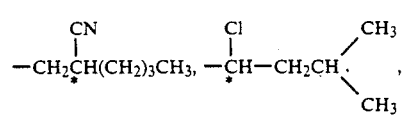
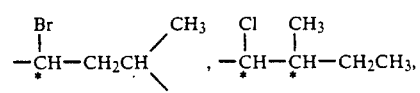
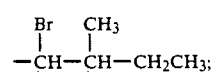
as $-R^5-R^6$ of the above (c),
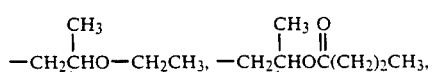
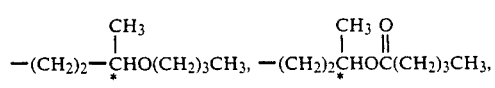
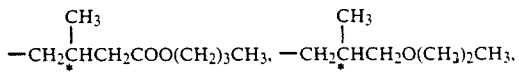
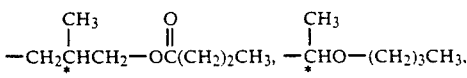
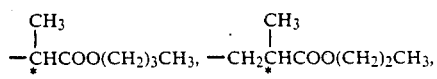
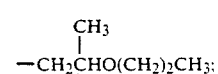
as $-R^7-R^8$ of the above (d),
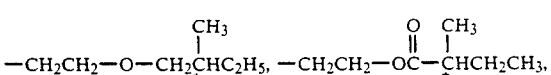
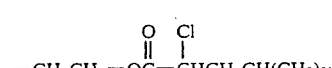
as $-R^5-R^9$ of the above (e),
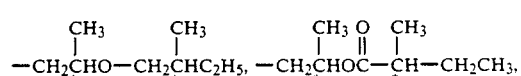
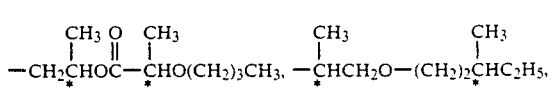

-continued
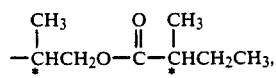
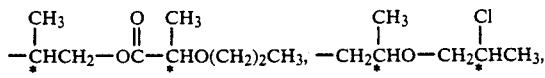
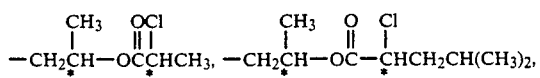
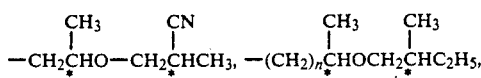
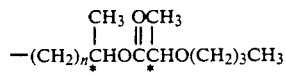
as the above (f),
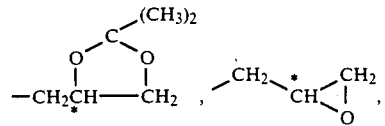
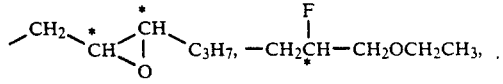
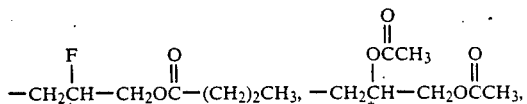
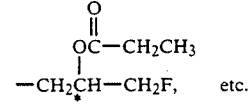 etc.
Representative compounds among those of the formula (I), and their phase transition points, spontaneous polarization values (Ps) and tilt angles are shown in Table 1. In addition, the symbol "?" in the table indicates that correct melting points are not known.

TABLE 1

| Compound No. | In formula (I) R¹ | R² | X | Y | Absolute configuration | Phase transition point (°C.) | $P_s(l)$ (nC/cm²) | Tilt angle (°) |
|---|---|---|---|---|---|---|---|---|
| 1 | CH₃—(CH₂)₆— | —OCH₂CHCH₂CH₃ (CH₃, *) | H | H | S | Cr.80 S₅.100 S₄.137.5 S₃.155.8 Sc*.174 S₄.183.3 I | | |
| 2 | CH₃—(CH₂)₅— | —O—(CH₂)₅CHCH₂CH₃ (CH₃, *) | H | H | S | Cr.125.0 S₂.170.0 Sc*.194.2 I | | |
| 3 | CH₃—(CH₂)₆— | —O—(CH₂)₅CHCH₂CH₃ (CH₃, *) | H | H | S | Cr.120.0 S₂.168.0 Sc*.192.5 I | | |
| 4 | CH₃—(CH₂)₅— | —O—CH₂—CH—(CH₂)₅CH₃ (F, *) | H | H | S | Cr.82.5 S₂.123.9 S₁.190.1 S₄.205.6 I | 65 | 25.2 |
| 5 | CH₃—(CH₂)₅— | —O—CH₂CHO(CH₂)₃—CH₃ (CH₃, *) | H | H | R | Cr.55.3 S₂.108.7 Sc*.138.0 I | 41 | 38.5 |
| 6 | CH₃—(CH₂)₆— | —O—CH₂CHO—(CH₂)₅—CH₃ (CH₃, *) | H | H | R | Cr.52.4 S₂.68.4 S₁.101.8 Sc*.130.6 I | 36 | 37.5 |
| 7 | CH₃—(CH₂)₆ | —OC—(CH₂)₃CHCH₂CH₃ (O=, CH₃, *) | H | H | S | Cr.? S₂.147.0 Sc*.193.4 I | | |
| 8 | CH₃—(CH₂)₅ | —OC—CHO—(CH₂)₂CH₃ (O=, CH₃, *) | H | H | R | Cr.110.0 S₃.116 S₂.132 Sc*.161.4 I | | |
| 9 | CH₃—(CH₂)₆— | —OC—CH—CH—CH₂CH₃ (O=, Cl, CH₃, *) | H | H | S,S | Cr.100 (S₆.83 S₅.97) S₄.117.5 S₃.126.5 Sc*.159.3 S₄.168.6 I_SO | 141 | 33.5 |
| 10 | CH₃—(CH₂)₄— | —OCH₂CHOC—(CH₂)₃CH₃ (CH₃, O=, *) | H | H | S | Cr.88.3 S₃ 108.5 Sc* 126.0 S₄ 130.3 I | 189 | 33.5 |
| 11 | CH₃—(CH₂)₅— | —OCH₂CHOC—(CH₂)₃CH₃ (CH₃, O=, *) | H | H | S | Cr.98.0 S₃.106.0 Sc*.123.8 S₄.124.0 I | 229 | 36.3 |

TABLE 1-continued

| Compound No. | In formula (I) R¹ | R² | X | Y | Absolute configuration | Phase transition point (°C.) | Ps(1) (nC/cm²) | Tilt angle (°) |
|---|---|---|---|---|---|---|---|---|
| 12 | CH₃—(CH₂)₈— | $\text{—OCH}_2\overset{*}{\text{CHO}}\underset{\underset{\text{CH}_3}{\|}}{\overset{\overset{\text{O}}{\|}}{\text{C}}}\text{—(CH}_2)_2\text{CH}_3$ | H | H | S | Cr.81.0 S₂.104.3 Sc*.125.8 I | 206 | 38.1 |
| 13 | CH₃—(CH₂)₈— | $\text{—OCH}_2\overset{*}{\text{CHOC}}\underset{\underset{\text{CH}_3}{\|}}{\overset{\overset{\text{O}}{\|}}{}}\text{—(CH}_2)_3\text{CH}_3$ | H | H | S | Cr.82.9 S₂.101.2 Sc*.121.7 I | 208 | 38.5 |
| 14 | CH₃—(CH₂)₄— | $\text{—OCH}_2\overset{*}{\text{CHOC}}\underset{\underset{\text{CH}_3}{\|}}{\overset{\overset{\text{O}}{\|}}{}}\text{—CH}_2\text{CHCH}_2\text{CH}_3$ | H | H | S,S | Cr.90.6 Sc*.118.2 I | 273 | 37.5 |
| 15 | CH₃—(CH₂)₄— | $\text{—OCH}_2\overset{*}{\text{CHOC}}\underset{\underset{\text{CH}_3}{\|}}{\overset{\overset{\text{O}}{\|}}{}}\text{—CHO—(CH}_2)_2\text{CH}_3$ | H | H | S,S | Cr.76.2 Sc*.101.0 S_A.113.3 Ch.114.9 I | 243 | 32.5 |
| 16 | CH₃—(CH₂)₄— | $\text{—O—CH}_2\overset{*}{\text{CHOCCHO}}\text{—O—(CH}_2)_3\text{CH}_3$ | H | H | S,S | Cr.76.0 Sc*.93.4 S_A.111.1 I | 245 | 32.5 |
| 17 | CH₃—(CH₂)₄— | $\text{—O—CH}_2\overset{*}{\text{CHOCCHO}}\text{—(CH}_2)_3\text{CH}_3$ | H | H | S,R | Cr.35.2 (S₃.28.0) Sc*.88.8 S_A.92.4 I | | 36.8 |
| 18 | CH₃—(CH₂)₅— | $\text{—OCH}_2\overset{*}{\text{CHOCCHO}}\text{—(CH}_2)_2\text{CH}_3$ | H | H | S,S | Cr.75.1 Sc*.100.7 S_A.105.6 Ch.109.2 I | 276 | 37.0 |
| 19 | CH₃(CH₂)₅— | $\text{—OCH}_2\overset{*}{\text{CHO—C—CHO}}\text{—(CH}_2)_3\text{CH}_3$ | H | H | S,S | Cr.67.6 Sc*.94.0 S_A.106.1 I | 262 | 35.0 |
| 20 | CH₃—(CH₂)₆— | $\text{—OCH}_2\overset{*}{\text{CHOC}}\text{—CHO(CH}_2)_3\text{CH}_3$ | H | H | S,R | Cr.54.5 Sc*.92.5 I | 165(2) | 35.5 |
| 21 | CH₃—(CH₂)₆— | $\text{—OCH}_2\overset{*}{\text{CHOC}}\text{—CHO(CH}_2)_2\text{CH}_3$ | H | H | S,S | Cr.73.5 Sc*.104.2 Ch.111.2 I | 256 | 37.0 |

TABLE 1-continued

| Compound No. | In formula (I) R¹ | R² | X | Y | Absolute configuration | Phase transition point (°C.) | $P_S^{(1)}$ (nC/cm²) | Tilt angle (°) |
|---|---|---|---|---|---|---|---|---|
| 22 | CH₃—(CH₂)₆— | —OCH₂CHOC—CHO(CH₂)₃CH₃ with CH₃, O, CH₃ | H | H | S,S | Cr.63.5 Sc*.97.8 S_A.108.8 I | 243 | 34.5 |
| 23 | CH₃—(CH₂)₈— | —OCH₂CHOC—CHO(CH₂)₃CH₃ with CH₃, O, CH₃ | H | H | S,S | Cr.70.1 Sc*.102.7 S_A.107.9 Ch.109.5 I | 243 | 38.4 |
| 24 | CH₃—(CH₂)₈— | —OCH₂CHOC—CHO(CH₂)₃CH₃ with CH₃, O, CH₃ | H | H | S,S | Cr.68.9 Sc*.107.0 I | 219 | 36.3 |
| 25 | CH₃—(CH₂)₅— | —OCH₂CHOC—CHCH₂CH₃ with CH₃, O, CH₃ | H | H | S,S | Cr.107.0 Sc*.112.0 I | 281 | 40.5 |
| 26 | CH₃—(CH₂)₆— | —OCH₂CHOC—CHCH₂CH₃ with CH₃, O, CH₃ | H | H | S,S | Cr.101.0 Sc*.113.1 I | 274 | 40.0 |
| 27 | CH₃—(CH₂)₈— | —OCH₂CHOC—CHCH₂CH₃ with CH₃, O, CH₃ | H | H | S,S | Cr.92.3 Sc*.108.6 Ch.110.8 I | 228 | 39.7 |
| 28 | CH₃—(CH₂)₅— | —OCH₂CHCH₂OC(CH₂)₂CH₃ with CH₃, O | H | H | R | Cr.? S₅.89 S₄.114 S₃.132 Sc*.145.0 S_A.145.5 I | 15 | 29.9 |
| 29 | CH₃—(CH₂)₅— | —OCH₂CHCH₂OC—CH₂OCH₂CH₃ with CH₃, O | H | H | R | Cr.63 S₄.77.6 S₃.122.3 Sc*.132.3 S_A.138.8 I | 21⁽²⁾ | 25.1 |
| 30 | CH₃—(CH₂)₅— | —OCH₂CHCH₂OC—CHO(CH₂)₂CH₃ with CH₃, O, CH₃ | H | H | R,S | Cr.? S₄.62.0 S₃.99.0 Sc*.116.0 S_A.117.4 I | 40⁽²⁾ | 31.3 |
| 31 | CH₃—(CH₂)₅— | —O—CHCOOEt with CH₃ | H | H | R | Cr.? Sc* 74.0 Ch 80.0 I | 94 | 35.0 |
| 32 | CH₃—(CH₂)₅— | —COCH(CH₂)₅CH₃ with O, CH₃ | H | H | R | Cr.57.4 S₄ 80.0 S₃ 90.3 Sc* 94.0 S_A 118.5 I | 96 | 22.7 |

TABLE 1-continued

| Compound No. | In formula (I) R¹ | R² | X | Y | Absolute configuration | Phase transition point (°C.) | Ps(I) (nC/cm²) | Tilt angle (°) |
|---|---|---|---|---|---|---|---|---|
| 33 | CH₃—(CH₂)₅— | —OCH₂—CH*—CH₂—O—C(CH₃)(CH₃)—O (dioxolane) | H | H | R | Cr.? S₃ 176.7 Sc* 185.5 S_A 192.6 I | | |
| 34 | CH₃—CH₂CH₂CH*CH₂O— (CH₃) | —(CH₂)₃CH₃ | H | H | S | Cr.? S_H* 118.5 S_G* 139.2 S_F* 144.4 S_B 158.7 Sc* 165.8 S_A 191.4 I | | |
| 35 | CH₃CH₂CH*CH(CH₂)₅O— (CH₃) | —(CH₂)₃CH₃ | H | H | S | Cr.61 S₅ 98.8 S_4 102.5 S₃ 170.0 Sc* 182.3 S_A 196.3 I | | |
| 36 | CH₃—(CH₂)₅CHCH₂O— (F) | —(CH₂)₇CH₃ | H | H | S | Cr.75.4 S₃ 106.0 S_B 153.7 Sc* 158.5 S_A 183.3 I | | |
| 37 | CH₃CH₂CH(CH₂)₄CO— (CH₃) (O) | —(CH₂)₃CH₃ | H | H | S | Cr.? S_G* 111.3 S_F* 152.4 S_B 182.8 S_A 207.0 I | | |
| 38 | CH₃(CH₂)₅OCHCH₂O— (CH₃) | —(CH₂)₃CH₃ | H | H | R | Cr.50.4 S_B 135.2 S_A 149.1 I | | |
| 39 | CH₃—CHCH₂O— (OH) | —(CH₂)₃CH₃ | H | H | S | Cr.135.4 S_A 189.6 Ch.198.3 I | | |
| 40 | CH₃—(CH₂)₃CO—CHCH₂O— (O)(CH₃) | —(CH₂)₃CH₃ | H | H | S | Cr.81.0 S_B 137.6 S_A 149.7 Ch | | |
| 41 | CH₃—(CH₂)₃OCHCO—CHCH₂O— (CH₃)(O)(CH₃) | —(CH₂)₃CH₃ | H | H | S,S | Cr.103.4 S_B 106.8 S_A 127.8 I | | |
| 42 | CH₃—(CH₂)₃OCHCO—CHCH₂O— (CH₃)(O)(CH₃) | —(CH₂)₇CH₃ | H | H | S,S | Cr.107.0 S_A 114.4 I | | |

TABLE 1-continued

| Compound No. | R¹ | R² | X | Y | Absolute configuration | Phase transition point (°C.) | Ps[1] (nC/cm²) | Tilt angle (°) |
|---|---|---|---|---|---|---|---|---|
| 43 | CH₃<br>\|<br>CH₃(CH₂)₅CHO— | —(CH₂)₃CH₃ | F | H | R | Cr.84.3 S₄.117.3 I | | |
| 44 | CH₃<br>\|<br>CH₃CH₂CH(CH₂)₄O— | —(CH₂)₃CH₃ | F | H | S | Cr.69 (S₄.53 S₃.57) Sc*.130.7 S₄.175.2 I | | |
| 45 | CH₃<br>\|<br>CH₃CH₂CH(CH₂)₅O— | —(CH₂)₃CH₃ | F | H | S | Cr.52 (S₅.37 S₄.39) S₃.105 Sc*.134.4 S₄.197.4 I | | |
| 46 | CH₃  O<br>\|   ‖<br>CH₃CH₂CH(CH₂)₄CO— | —(CH₂)₃CH₃ | F | H | S | Cr.? S$_F$* 117.2 Sc*.131.5 S₄.182.0 I | | |
| 47 | CH₃ O<br>\|  ‖<br>CH₃(CH₂)₃OCH—CO— | —(CH₂)₃CH₃ | F | H | S | Cr.43.5 S₃.89.0 Sc*.95.7 S₄.160.2 I | | |
| 48 | O  CH₃<br>‖   \|<br>CH₃(CH₂)₂CO—CHCH₂O— | —(CH₂)₃CH₃ | F | H | S | Cr.71.3 S₂.90.8 S₄.132.2 I | | |
| 49 | F<br>\|<br>CH₃(CH₂)₅CHCH₂O— | —(CH₂)₃CH₃ | F | H | S | Cr.97.1 S₄.181.0 I | | |

Note:
A blank (no numeral figure) in the column of Ps indicates either a case where no SC* phase was exhibited or a case where no measurement was carried out or Ps value was too small.
[1]The measurement value at a temperature which is lower by 10° C. than the upper limit temperature of SC* phase.
[2]The measurement value at a temperature which is lower by 5° C. than the upper limit temperature of SC* phase.

The compound of the formula (I) of the present invention can be prepared as follows:

1) In the case of the formula (I) wherein $R^1$ represents an optically inactive alkyl group or alkoxy group and $R^2$ represents an optically active group:

a) when $R^2$ is represented by $R^3$ (an alkyl group of 4 to 15 carbon atoms having methyl or ethyl branch),

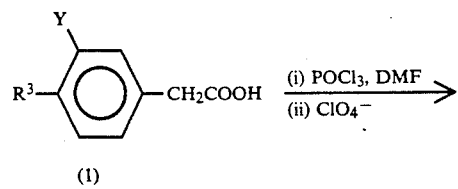

(1)

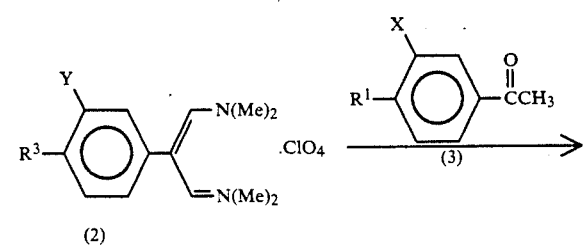

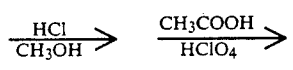

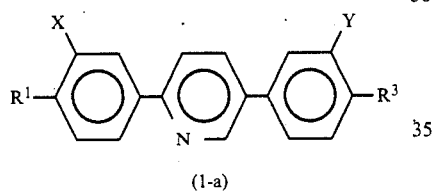

(1-a)

b) when $R^2$ is represented by $OR^3$,
i) when $R^1$ represents an alkyl group,

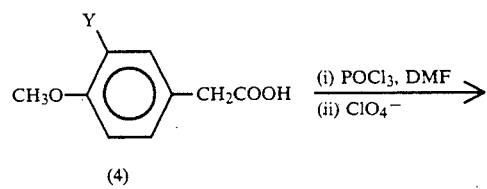

(4)

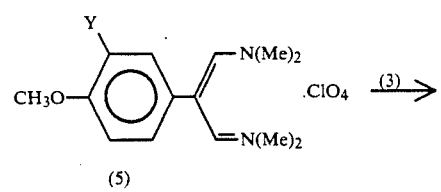

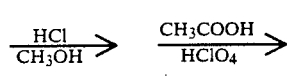

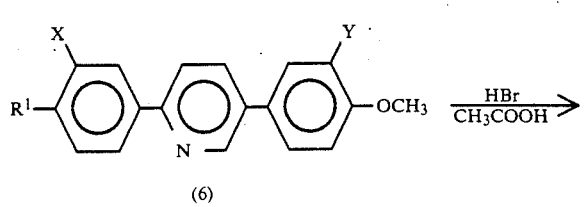

(6)

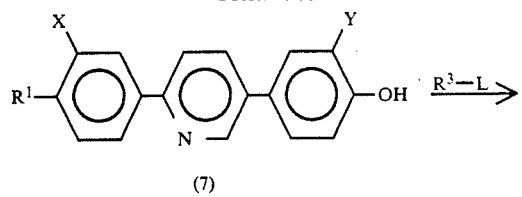

(7)

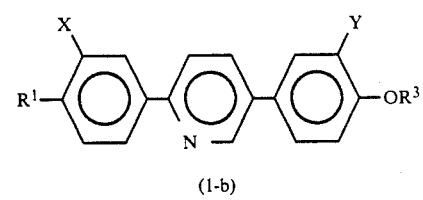

(1-b)

ii) when $R^1$ represents an alkoxy group,

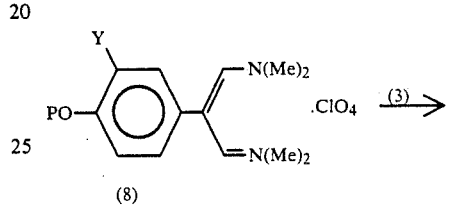

(8)

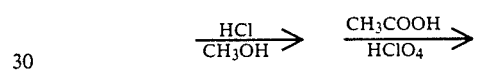

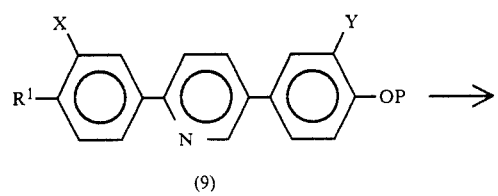

(9)

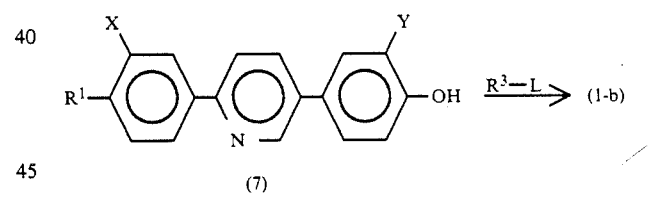

(7)

c) when $R^2$ is represented by

$$-\mathrm{OCR}^3,\overset{\mathrm{O}}{\underset{\|}{}}$$

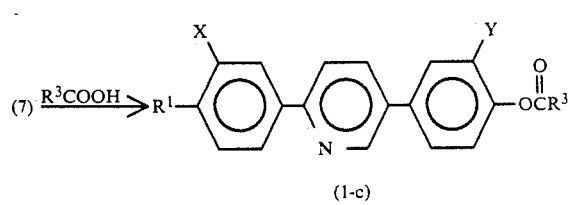

(1-c)

d) when $R^1$ is represented by

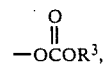

$$-\mathrm{OCOR}^3,\overset{\mathrm{O}}{\underset{\|}{}}$$

(7) 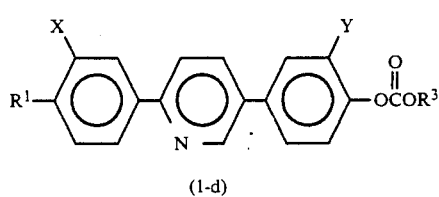

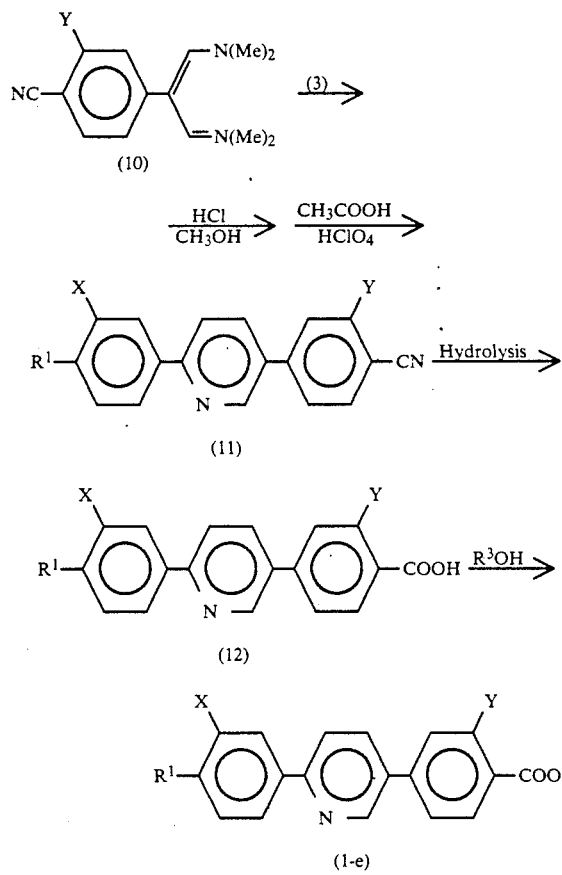

e) when R² is represented by —COOR³, f) when R² is represented by

(7) 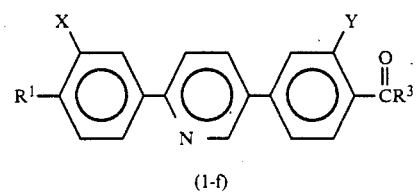

g) when R² is represented by R⁴ (a halogenated alkyl group or a cyanogenated alkyl group), preparation is carried out as in a); when R² is represented by OR⁴, it is carried out as in b); when R² is represented by

it is carried out as in c); when R² is represented by

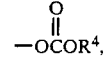

it is carried out as in d); when R² is represented by —COOR⁴, it is carried out as in e); and when R² is represented by

it is carried out as in f);

h) when R² is represented by —R⁵—R⁶ (wherein R⁵ represents an optically active alkylene group of 3 to 12 carbon atoms and —R⁶ represents an alkoxy group, an alkanoyl group an alkanoyloxy group, an alkoxycarbonyl group or an alkoxycarbonyloxy group each of 1 to 12 carbon atoms), preparation is carried out as in a); when R² is represented by —OR⁵—R⁶, preparation is carried out as in b); when R² is represented by

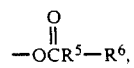

preparation is carried out as in c); when R² is represented by

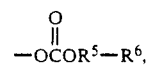

preparation is carried out as in d); and when R² is represented by —COOR⁵—R⁶, preparation is carried out as in f);

i) when R² is represented by —R⁷—R⁸ (wherein R⁷ represents an optically inactive alkylene group and R⁸ represents

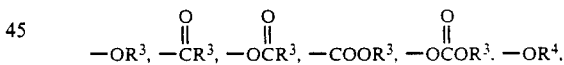

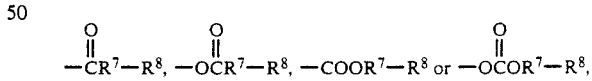

preparation is carried out as in h);

j) when R² is represented by —R⁵—R⁹ (wherein —R⁹ represents —R⁸ and

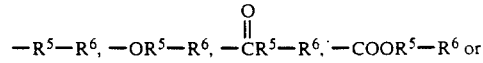

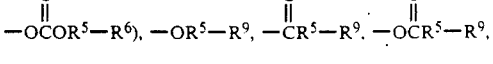

preparation is carried out as in h).

2) In the case of the formula (I) wherein $R^1$ represents an optically active group and $R^2$ represents an optically inactive alkyl group or alkoxy group, preparation is possible as in 1) a) to j) by replacing $R^1$ and $R^2$ in 1) by each other.

Since the compound of the present invention mostly exhibits a tilted smectic phase, it is suitable as a component for ferroelectric liquid crystals. Ferroelectric properties are exhibited in the respective phases of SC*, SI*, SF*, SG*, SJ*, SH* and SK*, as described above. The properties of exhibiting tilted smectic phase of the compound of the present invention are suitable for ferroelectric liquid crystal materials.

Further, the compound of the present invention is characterized in a large tilt angle. In the case of ferroelectric liquid crystals, the tilt angle of those having SA phase on the higher temperature side relative to SC* phase is generally 30° or less, and it is said that those having a tilt angle exceeding 30° have no SA phase.

As seen from Table 1, those having no SA phase on the higher temperature side relative to SC* have a large tilt angle exceeding 30° (see compound Nos. 5, 6, 12, 13, 14, 21, 24, 25, 26 and 27), while even those having SA phase often have a large tilt angle (see compound Nos. 10, 11, 15, 16, 17, 18, 19, 22, etc.).

As to the property of exhibiting a large tilt angle of the compound, even when the compound is used as a component for liquid crystal compositions, the property is reflected in the resulting compositions. Namely, when the compound of the present invention is used, it is possible to enlarge a tilt angle even in the case of compositions having SA phase. At present, as the driving mode of ferroelectric liquid crystals, birefringence mode and guest-mode are mentioned, and in the case of birefringence mode, a tilt angle of 22.5° and in the case of guest-host mode, a tilt angle of 45° are the best values required in the aspect of contrast, respectively. At present, however, compounds having a large tilt angle are not found so much; hence it is seen that the compound of the present invention is effective.

The compound of the present invention includes those which exhibit no ferroelectric liquid crystal phase by themselves, but when used as a component for ferroelectric liquid crystal compositions, have a large spontaneous polarization value (Ps) exhibited. For example, Compound No. 41 exhibits no ferroelectric liquid crystal phase by itself, but when added to an achiral smectic liquid crystal composition, exhibits a Ps value as large as 21.2 $nC/cm^2$. Further, as to the response time, a high-speed response rate of 28 μsec at 25° C. is also obtained (Example 9).

Further, since the compound of the formula (I) of the present invention has an optically active carbon atom, it has a capability of inducing a twisted structure when added to a nematic liquid crystal. Since a nematic liquid crystal having a twisted structure, i.e. a chiral nematic liquid crystal, does not form the so-called reverse domain, the compound of the formula (I) is usable as a agent for preventing the reverse domain from forming.

Further, the compound of the present invention is not limited only to the above-mentioned function as an agent for preventing the reverse domain from forming, but the pitch length of the cholesteric phase induced by adding the compound in a small quantity (about 1% by weight) to a nematic liquid crystal is as very short as about 10 μm; hence the compound is also very effective as a chiral additive for nematic display modes such as phase change mode, SBE mode, STN mode, etc.

The compound of the present invention will be described in more detail by way of Examples.

EXAMPLE 1

Preparation of (S)-2-(4-heptylphenyl)-5-(4-2′-methylbutyloxyphenyl)-pyridine a compound of the formula (I) wherein $R^1$ represents $C_7H_{15}$—; $R^2$ represents

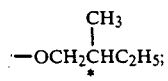

and X and Y are both hydrogen atom i.e. a compound expressed by the following structural formula:

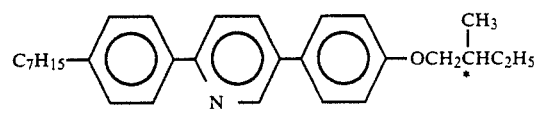

wherein the absolute configuration of the asymmetric carbon atom is in the form of S Compound No. 1

A) Phosphorus oxychloride (279.6 g, 1.8 mol) was dropwise added to anhydrous dimethylformamide (219.3 g, 3.0 mols) at 0° C., followed by portion-wise adding 4-methoxyphenylacetic acid (99.7 g, 0.6 mol) at −10° C., keeping the mixture at room temperature for one hour, agitating it at 60° C. for 2 hours and further at 80° C. for 4 hours, cooling the resulting material down to room temperature, dropwise adding an aqueous solution of magnesium perchlorate (133.8 g) dissolved in water (120 ml), filtering off deposited salt, washing it with ether and drying to obtain a salt (125 g, m.p.: 132.9°–134.4° C.).

4-Heptylacetophenone (23.7 g, 0.108 mol) was added to a solution of the above prepared salt (36.1 g, 0.108 mol) dissolved in anhydrous pyridine (60 ml), followed by slowly dropwise adding a sodium methylate solution obtained by reacting sodium (3 g) with methanol (50 ml) at room temperature, agitating the mixture at room temperature for 20 hours, distilling off pyridine, treating the residue with water, extracting the resulting material with toluene, distilling off toluene, recrystallizing the residue from methanol, dissolving the resulting crystals in methanol (100 ml), adding them to 2N-HCl (400 ml), agitating the mixture for 30 minutes, filtering off the residue, washing it with methanol, dissolving the resulting crystals in acetic acid (100 ml), slowly dropwise adding 60% perchloric acid (40 ml) to the solution, filtering off the residue, dissolving the resulting crystals in acetic acid (180 ml), adding ammonium acetate (50 g), refluxing the mixture for 2 hours, cooling the resulting material, pouring it in water, filtering off the residue and recrystallizing from EtOH to obtain 2-(4-heptylphenyl)-5-(4-methyloxyphenyl)pyridine (15 g) having a m p. of 109° C. and a clearing point of 212.9° C.

This 2-(4-heptylphenyl)-5-(4-methyloxyphenyl)pyridine (15 g, 0.042 mol) was dissolved in acetic acid (120 ml), followed by adding a 48% solution of hydrobromic acid (50 ml), refluxing the mixture for 30 hours, cooling the resulting material, pouring it in water, dissolving deposited crystals in 2N-NaOH aqueous solution on heating, adding acetic acid to obtain an acidic solution, filtering off the residue and recrystallizing from EtOH to obtain 2-(4-heptylphenyl)-5-(4-hydroxyphenyl)pyridine (10 g).

B) A mixture of this 2-(4-heptylphenyl)-5-(4-hydroxyphenyl)pyridine (8 g) with NaOH (1.7 g) was dissolved in ethanol (100 ml), followed by agitating the solution under reflux, dropwise adding thereto (S)-2-methylbutyl bromide (8 g), agitating the mixture under reflux for 8 hours, distilling off ethanol (about 80 ml), adding toluene (50 ml) to the residue, washing the toluene layer with a 2N-NaOH aqueous solution and further with water until the washing water became neutral, distilling off low boiling substances in the organic layer under reduced pressure and recrystallizing the residue from ethanol to obtain the objective compound which exhibited chiral smectic phase and the following phase transition points.

Cr —80° C.— S$_5$ —100° C.— S$_4$ —137.5° C.— S$_3$ —155.8° C.— SC* —174° C.— SA —183.3° C— I wherein S$_3$, S$_4$ and S$_5$ refer to a third smectic phase, a fourth smectic phase and a fifth smectic phase, which respectively appear when the temperature is lowered starting from the isotropic liquid (I) state. Similarly extending this order, Sx refers to a Xth smectic phase which appears when the temperature is lowered starting from I state.

EXAMPLE 2

Preparation of
(S)-2-(4-hexylphenyl)-5-(4-6'-methyloctyloxyphenyl)-pyridine a compound of the formula (I) wherein R$^1$ represents C$_6$H$_{13}$; R$_2$ represents

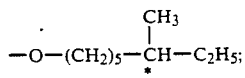

and X and Y each represent hydrogen atom i.e. a compound expressed by the formula

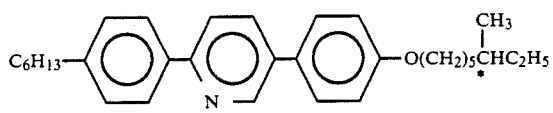

wherein the absolute configuration of the asymmetric carbon atom is in the form of S Compound No. 2

(S)-6-methyloctyl bromide (8 g) was dropwise added to a mixture of 2-(4-hexylphenyl)-5-(4-hydroxyphenyl)-pyridine (10 g) prepared in the same manner as in Example 1, KOH (2 g) and ethanol (200 ml) under reflux, followed by agitating the mixture for 6 hours, distilling off ethanol (about 150 ml), allowing the residue to cool down, extracting the residue with toluene, washing the resulting organic layer with 2N-NaOH aqueous solution and further with water until the washing water became neutral, distilling off toluene under reduced pressure and recrystallizing the residue from ethanol to obtain the objecting compound (12 g).

This compound exhibited chiral smectic phase and the transition phase temperatures were as follows:

Cr —125° C.— S$_2$ —170° C.— SC* —194.2° C.— I

EXAMPLE 3

Preparation of
(R)-2-(4-hexylphenyl)-5-(4-2'-propyloxypropionyloxyphenyl)pyridine a compound of the formula (I) wherein R$^1$ represents C$_6$H$_{13}$—; R$^2$ represents

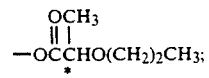

and X and Y each represent hydrogen atom i.e. a compound expressed by a structural formula

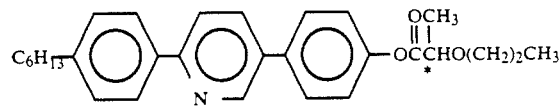

wherein the absolute configuration of the asymmetric carbon atom is in the form of R Compound No. 8

2-(4-Hexylphenyl)-5-(4-hydroxyphenyl)-pyridine (5 g) and 4-N,N-dimethylaminopyridine (5 g) prepared in the same manner as in Example 1A), 4-N,N-dimethylaminopyridine (hereinafter abbreviated to DMAP) (2 g) and dicyclohexylcarbodiimide (hereinafter abbreviated to DCC) (5.3 g) were dissolved in dichloromethane (200 ml), followed by dropwise adding to the solution, (R)-2-propyloxypropionic acid (5.3 g) prepared in the same manner as in Japanese patent application No. Sho 61-267206/1986, agitating the mixture at room temperature for 3 hours, filtering off deposited precipitates, washing the filtrate with 2N-NaOH aqueous solution and further with water until the washing water became neutral, distilling off low boiling substances in the organic layer and recrystallizing the residue from ethanol to obtain the objective compound (5 g). This product exhibited chiral smectic phase and the phase transition points were as follows:

Cr —110° C.— S$_3$ —116° C.— S$_2$ —132° C.— SC* —161.4° C.— I.

EXAMPLE 4

Preparation of
(S)-2-(4-heptylphenyl)-5-(4-6'-methyloctyloxyphenyl)-pyridine a compound of the formula (I) wherein R$^1$ represents C$_7$H$_{15}$—; and R$^2$ represents

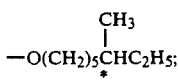

and X and Y each represent hydrogen atom i.e. a compound expressed by a structural formula

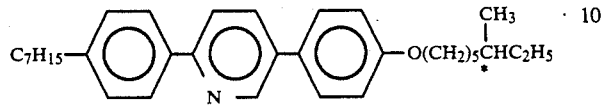

wherein the absolute configuration of the asymmetric carbon atom is in the S form Compound No. 3

Example 1 B) was repeated except that (S)-2-methylbutyl bromide used in Example 1 B) was replaced by (S)-6-methyloctyl bromide to obtain the objective compound. This product exhibited chiral smectic phase and its phase transition points were as follows:

Cr —120° C.— $S_2$ —168° C.— SC* —192.5° C.— I

EXAMPLE 5

Preparation of (S)-2-(4-heptylphenyl)-5-(4-5'-methylheptanoyloxyphenyl)pyridine a compound of the formula (I) wherein $R^1$ represents $C_7H_{15}$—; and $R^2$ represents

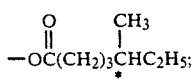

and X and Y each represent hydrogen atom i.e. compound expressed by a structural formula

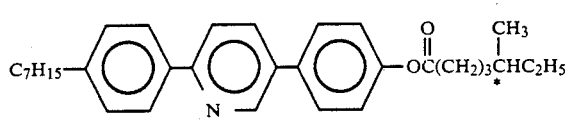

wherein the absolute configuration is in the S-form

Compound No. 7

2-(4-Heptylphenyl)-5-(4-hydroxyphenyl)pyridine (5 g), DCC (5 g) and DMAP (2 g) were dissolved in dichloromethane (100 ml), followed by adding (S)-5-methylheptanoic acid (3 g) to the solution, agitating the mixture at room temperature for 3 hours, filtering off deposited precipitates, washing the filtrate with 2N-NaOH aqueous solution an then with water until the washing water became neutral, distilling off the low boiling substances in the organic layer and recrystallizing the residue from ethanol to obtain the objective compound (5 g). This product exhibited chiral, smectic phase and the phase transition points were as follows:

Cr —?— $S_2$ —147° C.— SC* —193.4° C.— I (the symbol "?" indicates "unidentified"; this applies to the subsequent).

EXAMPLE 6

Preparation of (S)-2-(4-2'-pentanoyloxypropyloxyphenyl)-5-(4-butylphenyl)pyridine a compound of the formula (I) wherein $R^1$ represents

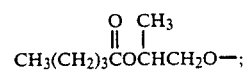

$R^2$ represents —$(CH_2)_3CH_3$; and X and Y each are hydrogen atom i.e. a compound expressed by a structural formula

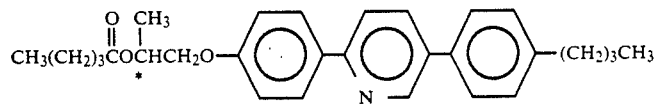

wherein the absolute configuration of the asymmetric carbon atom is in the S form Compound No. 40

A mixture of (S)-2-(4-2'-hydroxypropyloxyphenyl)-(4'-butylphenyl)pyridine (4 g) prepared from 2-(4-hydroxyphenyl)-5-(4-butylphenyl)pyridine in the same manner as in Japanese patent application No. 61-133269/1986, DCC (4 g) and DMAP (0.2 g) was dissolved in dichloromethane (50 ml), followed by dropwise adding pentanoic acid (1.5 g) to the solution, agitating the mixture at room temperature for 2 hours, filtering off deposited precipitates, washing the filtrate with N-NaOH aqueous solution and then with water until the washing water became neutral, distilling off the low boiling substances in the organic layer and recrystallizing the residue from ethanol to obtain the objective compound (3 g). This product exhibited chiral smectic phase and the phase transition points were as follows:

Cr —81.0° C.— SB —137.6° C.— SA —149.7° C.— I

EXAMPLE 7

Preparation of (2'S,2"S)-2-(4-2g-2"-butyloxypropanoyloxypropyloxyphenyl)-5-(4-butylphenyl)pyridine a compound of the formula (I) wherein $R^1$ represents

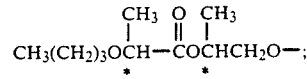

$R^2$ represents —$(CH_2)_3CH_3$; and X and Y each represent hydrogen atom i.e. a compound expressed by a structural formula

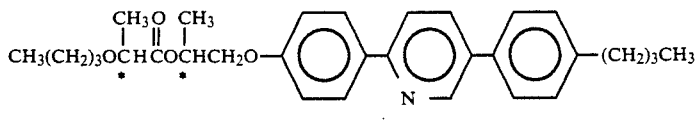

wherein the absolute configuration of the asymmetric carbon atom is in the form of (2'S,2"S).

Compound No. 41

Example 6 was repeated except that pentanoic acid used in Example 6 was replaced by S-2-butyloxypropionic acid prepared in the same manner as in Japanese patent application No. Sho 61-267206/1986 to obtain the objective compound. This product exhibited smectic phase and the phase transition points were as follows:

$$Cr \xrightarrow{103.4° C.} SB \xrightarrow{106.8° C.} SA \xrightarrow{127.8° C.} I$$

EXAMPLE 8 (Use example 1)

Compound No. 22 had a spontaneous polarization value of 425 $nC/cm^2$ as measured according to Sawyer-Tower method and a tilt angle of 41.5°. This compound was filled in a cell of 2 μm thickness provided with transparent electrodes obtained by applying PVA as an aligning agent and rubbing the resulting surface to subject it to a parallel aligning treatment, followed by placing this cell between two crossed polarizers and impressing a square wave having a height of 10V. As a result, change in the intensity of transmitted light was observed. The response time sought from the change in the intensity of transmitted light at that time was 42 μsec at 67.8° C.

EXAMPLE 9 (Use example 2)

The following composition consisting of achiral substances and exhibiting SC phase was prepared:

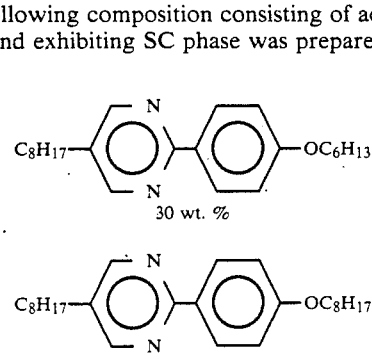

30 wt. %

20 wt. %

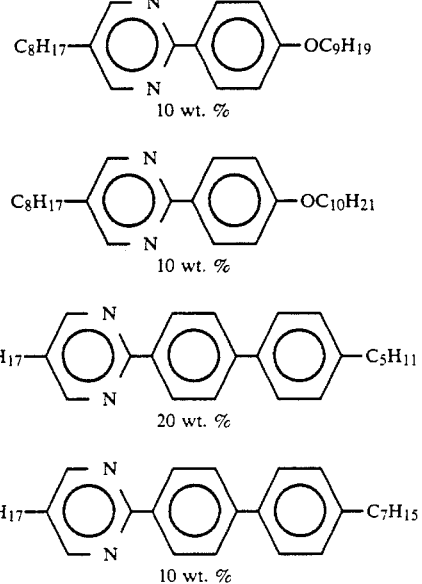

This composition exhibited the following phase transition points:

$$Cr \xrightarrow{4° C.} SC \xrightarrow{65° C.} SA \xrightarrow{79° C.} N \xrightarrow{90° C.} I$$

To this composition was added the following compound of the present invention (Compound No. 41) in 20% by weight:

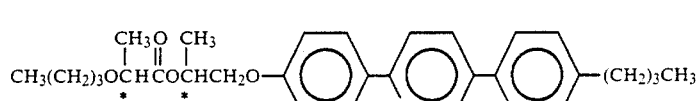

As a result, SC* phase exhibiting ferroelectric properties at 45° C. or lower appeared. This composition had a spontaneous polarization value of 21.2 $nC/cm^2$ at 25° C. and a tilt angle of 17°.

The response time of this composition sought under the same conditions as in Example 8 was 28 μsec at 25° C.

As described above, it has been found that when the compound of the present invention is added to a compound (or composition) having SC phase exhibiting no ferroelectric properties, a ferroelectric liquid crystal composition exhibiting very high-speed response properties is obtained.

EXAMPLE 10 (Use example 3)

To the above composition A was added the following compound of the present invention (Compound No. 22):

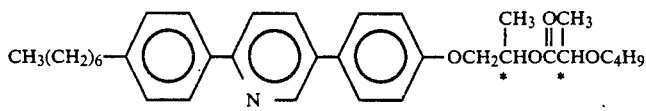

in 20% by weight. As a result, SC* phase exhibiting ferroelectric properties at 70.7° C. or lower appeared. This composition had a spontaneous polarization value of 37.8 nC/cm² and a tilt angle of 24.3° at 25° C. The response time of this composition was sought under the same conditions as in Example 8 to give 45 μsec at 25° C.

EXAMPLE 11 (Use example 4)

A nematic liquid crystal composition consisting of

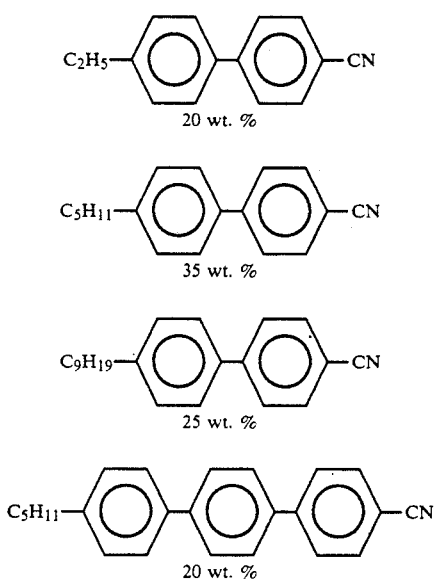

was filled in a cell provided with electrodes obtained by applying polyvinyl alcohol (PVA) as a aligning agent and rubbing the resulting surface to subject it to a parallel aligning treatment and having a distance between the electrodes of 10 μm to prepare a TN mode display cell, which was then observed under a polarizing microscope. As a result, a reverse twist domain was observed to be formed.

To this nematic liquid crystal composition wa added the following compound of the present invention (Compound No. 45):

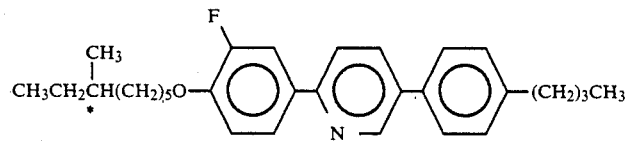

in 1% by weight, and the composition was similarly observed with a TN mode cell. As a result, the reverse twist domain was dissolved and a uniform nematic phase was observed.

EXAMPLE 12 (Use example 5)

To a nematic liquid crystal composition (ZLI-1132 made by Merck Company) was added a compound of the present invention (Compound No. 40) in 1% by weight to prepare a chiral nematic composition. This chiral nematic liquid crystal composition was filled in a wedge type cell subjected to a parallel aligning treatment and the resulting cell was observed under a polarizing microscope. As a result, the following helical pitches were observed:

| Temperature (°C.) | 20 | 30 | 40 | 50 | 60 | 70 |
|---|---|---|---|---|---|---|
| Pitch length (μm) | 11.1 | 11.2 | 11.3 | 11.4 | 11.5 | 11.1 |

As described above, the temperature dependency of the pitch was very flat; hence it has been found that the compound of the present invention is a superior agent for adjusting the pitch of chiral nematic liquid crystal compositions.

What we claim is:

1. An optically active 2,5-diphenylpyridine expressed by the formula

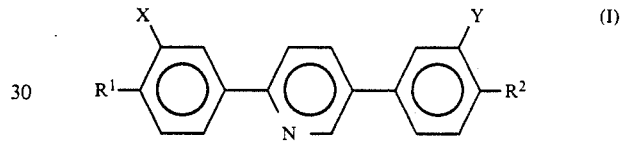

wherein one of $R^1$ and $R^2$ represents an alkyl group or an alkoxy group, each of 4 to 10 carbon atoms, and the other thereof represents an optically active group selected from the group consisting of

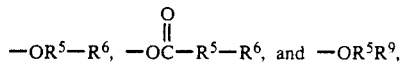

$R^5$ represents an optically active alkylene group of 2 to 12 carbon atoms;
$R^6$ represents an alkoxy group, an alkanoyl group, an alkanoyloxy group, an alkoxycarbonyl group or an alkoxycarbonyloxy group, each of 1 to 12 carbon atoms; and
$R^9$ represents a group expressed by

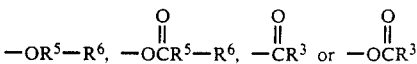

wherein
$R^5$ and $R^6$ are as defined above; and $R^3$ represents an optically active alkyl group of 4 to 15 carbons having a methyl or ethyl branch
X represents hydrogen or halogen; and
Y represents hydrogen.

2. An optically active 2,5-diphenylpyridine according to claim 1 wherein said one of R¹ and R² represents an alkyl group of 4 to 10 carbon atoms, X represents hydrogen or fluorine and Y represents hydrogen.

3. An optically active 2,5-diphenylpyridine according to claim 1 wherein said one of R¹ and R² represents an alkyl group of 4 to 10 carbon atoms and the other represents $$-OR^5-R^6 \text{ or } -O-\overset{O}{\underset{\|}{C}}-R^5-R^6 \text{ wherein } -R^5-R^6 \text{ represents}$$

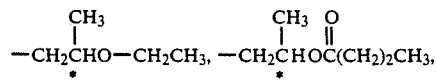

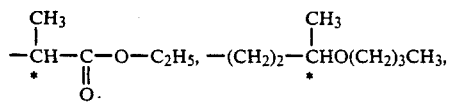

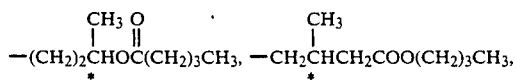

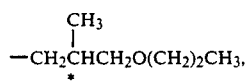

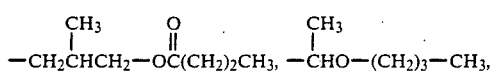

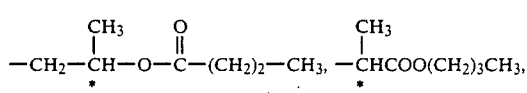

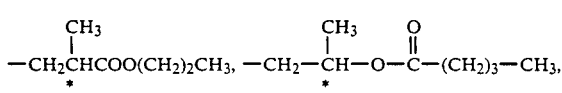

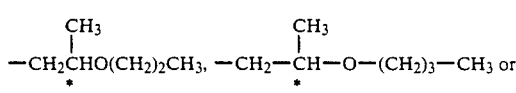

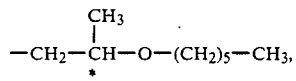

X represents hydrogen or fluorine and Y represents hydrogen.

4. An optically active 2,5-diphenylpyridine according to claim 1 wherein said one of R¹ and R² represents an alkyl group of 4 to 10 carbon atoms and the other represents $-OR^5-R^9$ represents

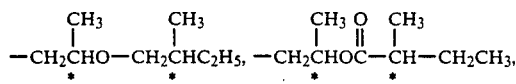

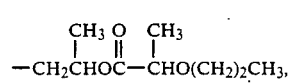

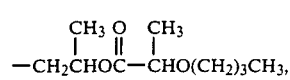

-continued $$-\overset{CH_3}{\underset{*}{CHCH_2}}O-(CH_2)_2\overset{CH_3}{\underset{*}{CHC_2H_5}},$$

$$-\overset{CH_3}{\underset{*}{CHCH_2}}O-\overset{O}{\underset{\|}{C}}-\overset{CH_3}{\underset{*}{CHCH_2CH_3}},$$

$$-\overset{CH_3}{\underset{*}{CHCH_2}}-O\overset{O}{\underset{\|}{C}}-\overset{CH_3}{\underset{*}{CHO(CH_2)_2CH_3}}, -\overset{CH_3}{\underset{*}{CH_2CHO}}-\overset{Cl}{\underset{*}{CH_2CHCH_3}},$$

$$-\overset{CH_3}{\underset{*}{CH_2CH}}-\overset{OCl}{\underset{\|}{OCCHCH_3}}, -\overset{CH_3}{\underset{*}{CH_2CH}}-O\overset{O}{\underset{\|}{C}}-\overset{Cl}{\underset{*}{CHCH_2CH(CH_3)_2}},$$

$$-\overset{CH_3}{\underset{*}{CH_2CHO}}-\overset{CN}{\underset{*}{CH_2CHCH_3}}, \text{ or}$$

$$-CH_2-\overset{CH_3}{\underset{*}{CH}}-CH_2-O-\overset{O}{\underset{\|}{C}}-\overset{CH_3}{\underset{*}{CH}}-O(CH_2)_2CH_3,$$

X represents hydrogen or fluorine and Y represents hydrogen.

5. An optically active 2,5-diphenylpyridine according to claim 3 wherein said $-R^5-R^6$ represents

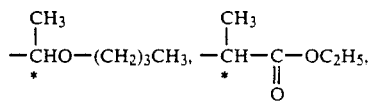

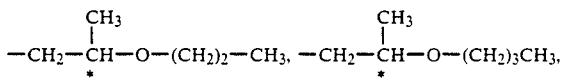

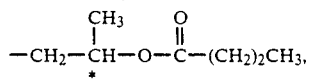

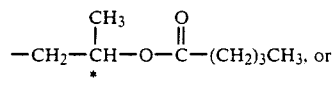

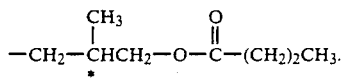

6. An optically active 2,5-diphenylpyridine according to claim 4 wherein said $-R^5-R^9$ represents

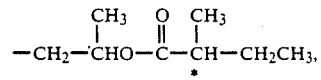

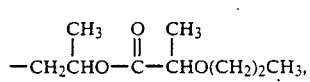

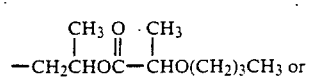

-continued

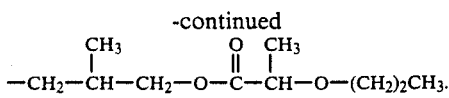

7. A liquid crystal composition comprising at least two components, at least one of which is an optically active 2,5-diphenylpyridine as set forth in claim 1.

8. A liquid crystal composition according to claim 7 exhibiting a chiral smectic phase.

9. A liquid crystal composition according to claim 7 exhibiting a chiral nematic phase.

10. An optically active 2,5-diphenylpyridine expressed by the formula

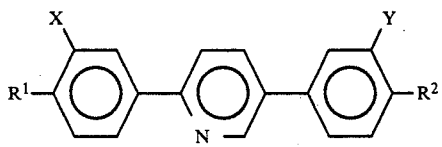

wherein one of $R^1$ and $R^2$ represents an alkyl group or an alkoxy group, each of 4 to 10 carbon atoms, and the other thereof represents an optically active group selected from the group consisting of

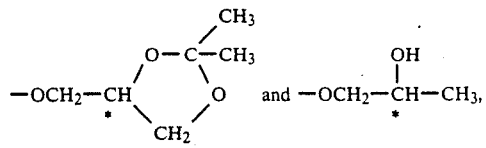

X represents hydrogen or halogen; and
Y represents hydrogen.

11. An optically active 2,5-diphenylpyridine according to claim 10 wherein said one of $R^1$ and $R^2$ represents an alkyl group of 4 to 10 carbon atoms, X represents hydrogen or fluorine and Y represents hydrogen.

12. A liquid crystal composition comprising at least two components, at least one of which is an optically active 2,5-diphenylpyridine as set forth in claim 10.

13. A liquid crystal composition according to claim 12 exhibiting a chiral smectic phase.

14. A liquid crystal composition according to claim 12 exhibiting a chiral nematic phase.

* * * * *